United States Patent [19]
Adkins et al.

[11] Patent Number: 5,942,151
[45] Date of Patent: Aug. 24, 1999

[54] POLYMERIC MDI COLOR

[75] Inventors: Rick L. Adkins; Clarence D. Blue, both of New Martinsville, W. Va.

[73] Assignee: Bayer Corporation, Pittsburgh, Pa.

[21] Appl. No.: 08/975,434

[22] Filed: Nov. 20, 1997

[51] Int. Cl.[6] .................................................. C08G 18/76
[52] U.S. Cl. .......................... 252/182.2; 560/332; 564/5; 564/6; 564/334
[58] Field of Search .......... 560/332; 252/182.2; 564/334, 5, 6

[56] References Cited

U.S. PATENT DOCUMENTS

| | | | |
|---|---|---|---|
| 1,973,724 | 9/1934 | Perkins | 564/5 |
| 3,253,031 | 5/1966 | Powers | 260/570 |
| 3,260,751 | 7/1966 | Powers et al. | 260/570 |
| 3,277,139 | 10/1966 | Powers | 260/453 |
| 3,277,173 | 10/1966 | Powers et al. | 260/570 |
| 3,362,979 | 1/1968 | Bentley | 260/453 |
| 3,496,229 | 2/1970 | Powers et al. | 260/570 |
| 3,517,062 | 6/1970 | Powers | 260/570 |
| 3,641,094 | 2/1972 | Arlt et al. | 260/453 PH |
| 3,912,600 | 10/1975 | Hatfield, Jr. et al. | 203/73 |
| 4,259,526 | 3/1981 | Dunlap et al. | 564/331 |
| 4,792,624 | 12/1988 | Hatfield, Jr. et al. | 564/333 |
| 5,312,971 | 5/1994 | Adkins et al. | 560/347 |

FOREIGN PATENT DOCUMENTS 154431  8/1974  Czechoslovakia .

*Primary Examiner*—Rachel Gorr
*Attorney, Agent, or Firm*—Joseph C. Gil; Noland J. Cheung

[57] ABSTRACT

A process for the production of polymethylene polyphenyl polyisocyanates is disclosed. The process comprises phosgenating the corresponding polyamines in solution in an inert organic solvent, removing excess phosgene, and stripping the solvent, the improvement wherein at least 0.00015 percent by weight of hydrazine or hydrazine derivative per 100 percent by weight of polyamine are added to the polyamines at any time prior to the stripping step.

4 Claims, No Drawings

POLYMERIC MDI COLOR

BACKGROUND OF THE INVENTION

Processes for the production of polymethylene polyphenyl polyamines and phosgenation of such polyamines to produce the corresponding polyisocyanates are well known in the art (see, e.g., U.S. Pat. Nos. 3,253,031, 3,260,751, 3,277,139, 3,277,173, 3,362,979, 3,496,229, 3,517,062, 3,641,094, 3,912,600 and 4,259,526).

In general, the process of producing the polyisocyanates includes the steps of phosgenating the polyamines in solution in an organic solvent, removing excess phosgene and then stripping the inert solvent. Some effort has been expended in reducing the color of the resultant polyisocyanates. U.S. Pat. No. 4,465,639 describes the addition of water prior to the solvent stripping step to reduce the color. U.S. Pat. No. 4,792,624 describes a specific polyamine recycling step during the aniline/formaldehyde reaction to cause a reduction in color of the corresponding polyisocyanate.

Czechoslovakian Patent 154,431 describes a method of isolating isomers of diaminodiphenylmethane using a water extraction process. The reference describes the use of deoxygenated water in the extraction and suggests that reducing agents should be added to the water in order to minimize staining of the isolated diamine.

U.S. Pat. No. 5,312,971 describes a process whereby a reducing agent such as borane-tetrahydrofuran added to the polyamines can result in reduction of color of the corresponding isocyanate.

SUMMARY OF THE INVENTION

A process for the production of polymethylene polyphenyl polyisocyanates is disclosed. The process comprises phosgenating the corresponding polyamines in solution in an inert organic solvent, removing excess phosgene, and stripping the solvent, the improvement wherein at least 0.00015 percent by weight of hydrazine or a hydrazine derivative is added to the polyamines at any time prior to the stripping step.

DESCRIPTION OF THE INVENTION

The present invention is directed to the discovery that a relatively small amount of hydrazine and/or its derivatives added to the polyamines can result in a significant reduction in the color of the corresponding polyisocyanate. More particularly, the present invention is directed to a process for the production of polymethylene polyphenyl polyisocyanates comprising phosgenating the corresponding polyamines in solution in an inert organic solvent, removing excess phosgene, and stripping said solvent, the improvement wherein at least 0.00015% by weight of the hydrazine and/or its derivatives is added to said polyamines at any time prior to said stripping step.

As is well known in the art, the polymethylene polyphenyl polyamines are prepared by reacting aniline and formaldehyde in the presence of an aqueous acid catalyst (generally hydrochloric acid). The polyamines are isolated from the reaction mixture by first adding an excess of a neutralizing agent (generally sodium hydroxide), and then removing any excess neutralizing agent, water and aniline. The hydrazine and/or derivatives of the present invention have been found to be effective in reducing the color of the corresponding polyisocyanate if they are added at any time following the addition of the neutralizing agent and before the stripping of the solvent used for phosgenation. Most effective results have been found where the addition of the hydrazine occurs prior to phosgenation of the polyamine.

The details of the production of the polymethylene polyphenyl polyamines and the phosgenation to the corresponding polyisocyanates are known and described, for example, in U.S. Pat. Nos. 3,253,031, 3,260,751, 3,277,139, 3,277,173, 3,362,979, 3,496,229, 3,517,062, 3,641,094, 3,912,600, 4,259,526, 4,465,639 and 4,792,624, the disclosures of which are herein incorporated by reference.

Substantially any hydrazine and/or its derivatives can be used herein. Useful additives include hydrazine, hydrazine hydrate, hydrazine hydro-chlorides, hydrazine and its salts, carbohydrazides and carbohydrazide derivatives. Specific additives include 4-Nitrophenyl-hydrazine, acetyl-hydrazine, acetyl phenyl hydrazine, 1-acetyl-2-phenyl hydrazine, benzoyl-hydrazine, benzylhydrazine dihydrochloride, 2-bromophenylhydrazine hydrochloride, 3-bromophenyl-hydrazine, 4-bromophenylhydrazine-hydrochloride, tert-butylphenylhydrazine, 4-n-butylphenylhydrazine hydrochloride, 4-tert-butylphenylhydrazine hydrochloride, N-a-(chloro-benzoyl)-p-methoxy-phenylhydrazine, 2-chloro-phenylhydrazine hydrochloride, 3-chloro-phenylhydrazine hydrochloride, 4-chlorophenyl-hydrazine hydrochloride, cyclohexyl methylhydrazine, symdibenzoyl-hydrazine, 2,3-dichloro-phenylhydrazine, 2,4-dichlorophenyl-hydrazine hydrochloride, 2,3-dichlorophenylhydrazine, 2,5-dichlorophenyl-hydrazine hydrochloride, 2,6-dichlorophenylhydrazine hydrochloride, 3,4-dichlorophenyl-hydrazine hydrochloride, 3,5-dichlorophenylhydrazine hydrochloride, 2,4-difluoro-phenylhydrazine hydrochloride, dihydrazine sulfate, 1,2-dimethyl-hydrazine dihydrochloride, 1,1-dimethylhydrazine (unsymmetrical), 2,3-dimethylphenylhydrazine hydrochloride, 2,4-dimethylphenylhydrazine hydrochloride, 2,5 dimethyl-phenylhydrazine hydrochloride, 2,6 dimethyl-phenylhydrazine hydrochloride, 3,4-dimethylphenylhydrazine hydrochloride, 3,5-dimethylphenylhydrazine hydrochloride, 2,4-dinitrophenylhydrazine, 1,1-diphenylhydrazine hydrochloride,(2-ethylphenyl)hydrazine hydrochloride, 4-ethylphenylhydrazine hydrochloride, 2-fluorophenylhydrazine hydrochloride, p-fluorophenyl hydrazine hydrochloride, 4-fluorophenyl hydrazine hydrochloride, anhydrous hydrazine, hydrazine base, hydrazine dihydrobromide, hydrazine dihydrochloride, hydrazine hydrate, hydrazine monoacetate, hydrazine monohydrobromide, hydrazine monohydrochloride, hydrazine mononitrate, hydrazine oxygen scavenger, hydrazine solution, carbohydrazide, 1,5-diphenylcarbazide, and 4-phenylsemicarbazide. The presently preferred additive is hydrazine hydrate.

The amount of additive added can vary over a wide range. In general, at least 0.00015% by weight of additive per 100% by weight of the polyamine should be added. The upper limit is dictated by economics. In general, amounts in excess of 10% by weight of additive per 100% of polyamine do not show any increased advantage.

The color of polymethylene polyphenyl polyisocyanates can be broken down into two main absorptions in the UV-Visible spectrum—430 nm and 520 nm. A color improvement is herein defined as an increase in the color number of a standard PMDI. A color number is defined as the ratio of the 430 nm to 520 nm absorbances.

The invention is further illustrated but is not intended to be limited by the following examples in which all parts and percentages are by weight unless otherwise specified.

EXAMPLES

Example 1
(PMDI Laboratory Standard)

PMDA (100 g) was dissolved in 500 ml MCB and purged with nitrogen. MCB (1.5 liters) was cooled to 0° C. and phosgene added at 2 mole/h for 1.5 hours. The phosgene flow was then reduced to 0.5 mole/h. The PMDA/MCB solution was added to the phosgene solution at 0° C. After complete addition, the phosgenation solution was slowly heated to 130° C. and maintained at this temperature for 1 h with phosgene. The PMDI/MCB solution was purged with nitrogen for 20 minutes and then the solvent was vacuum distilled to give the final PMDI product.

Example 2

PMDA (100 g) and 64% hydrazine hydrate (0.1 g) were stirred at 100° C. under nitrogen for 24 hours. The PMDA was then water washed and dried of water to remove residual hydrazine hydrate. The hydrazine level was measured at 1.5 ppm. The PMDA was then phosgenated as shown above.

Example 3

PMDA (100 g) and 64% hydrazine hydrate (0.1 g) were stirred at 100° C. under nitrogen for 24 hours. The PMDA was then phosgenated as shown in Example 1 above.

Examples 4–6

These examples were identical to Example 2 except for the hydrazine level.

Example 7

PMDA (100 g) and anhydrous hydrazine (0.9 g) were stirred at 100° C. under nitrogen for 24 hours. The PMDA was then phosgenated as shown in Example 1 above.

Example 8

PMDA (100 g) was dissolved in 500 ml MCB and purged with nitrogen. Hydrazine hydrate (0.7 g) was added to this solution and stirred for 5 minutes. This solution was then phosgenated as shown in Example 1 above.

Example 9

PMDA (100 g) was dissolved in 500 ml MCB and purged with nitrogen. MCB (1.5 liters) was cooled to 0° C. and phosgene added at 2 mole/h for 1.5 hours. The phosgene flow was then reduced to 0.5 mole/h. The PMDA/NMCB solution was added to the phosgene solution at 0° C. After complete addition, the phosgenation solution was slowly heated to reflux (about 128° C.). At this point 0.4 g of anhydrous hydrazine was added, and the reaction mixture was maintained at this temperature for 1 h with phosgene. The PMDI/MCB solution was purged with nitrogen for 20 minutes and then the solvent was vacuum distilled to give the final PMDI product.

Example 10
(Example using reducing agent from U.S. Pat. No. 5,312,971)

Borane-tetrahydrofuran complex (0.011 mole, 0.9 wt. %) was added to PMDA (100 g) and heated at 100° C. for 1 hour. Methanol (2 ml) was slowly added to neutralize residual complex, and the solution was heated to 100° C. under vacuum to remove low boilers. This PMDA was then phosgenated as shown in Example 1 above.

TABLE I

Effect of Hydrazine on PMDI Color

| Product | Hydrazine (wt. %) | Color Number |
|---|---|---|
| Example 1 | 0.0 | 2.2 |
| Example 2 | 0.00015 | 3.5 |
| Example 3 | 0.06 | 6.7 |
| Example 4 | 0.45 | 8.2 |
| Example 5 | 0.9 | 8.5 |
| Example 6 | 2.6 | 9.1 |
| Example 7 | 0.9 | 7.1 |
| Example 8 | 0.45 | 8.1 |
| Example 9 | 0.4 | 4.3 |
| Example 10 | 0.9 | 5.3 |
|  | borane-THF |  |

1) Examples 1–6 illustrate that color improves with increasing hydrazine concentration.
2) Example 7 illustrates that the color improvement is due to the presence of hydrazine, not from the water as suggested by U.S. Pat. No. 4,465,639.
3) Example 8 illustrates that hydrazine can be added to the PMDA/MCB solution immediately prior to phosgenation, rather than to an MDA storage vessel for 24 hr.
4) Example 9 illustrates that the hydrazine can be added during the phosgenation.
5) Example 10 illustrates that the preferred reducing agent from U.S. Pat. No. 5,312,971 is not as effective as hydrazine. For instance, the molar ratio of Example 10 vs. Example 3 is 5.8, which indicates that the concentration of borane-tetrahydrofuran is much higher. The color number ratio of Example 10 vs. Example 3, however, is 0.79. Therefore, at a much lower concentration, hydrazine hydrate gives better and improved color numbers when compared with borane-tetrahydrofuran.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of polymethylene polyphenyl polyisocyanates comprising phosgenating the corresponding polyamines in solution in an inert organic solvent, removing excess phosgene, and stripping said solvent, the improvement wherein at least 0.00015 percent by weight of an additive per 100 percent by weight of polyamine are added to said polyamines at any time prior to said stripping step, wherein said additive is hydrazine or a hydrazine derivative.

2. The process of claim 1, wherein said hydrazine derivative is selected from the group consisting of hydrazine hydrate, hydrazine hydrochlorides, hydrazine and its salts, carbohydrazides and carbohydrazide derivatives.

3. The process of claim 2, wherein said hydrazine derivative is selected from the group consisting of 4-Nitrophenylhydrazine, acetyl-hydrazine, acetyl phenyl hydrazine, 1-acetyl-2-phenyl hydrazine, benzoylhydrazine, benzylhydrazine dihydrochloride, 2-bromophenylhydrazine hydrochloride, 3-bromophenylhydrazine, 4-bromophenylhydrazinehydro-chloride, tert-butylphenylhydrazine, 4-n-butylphenylhydrazine hydrochloride, 4-tert-butylphenylhydrazine hydrochloride, N-a-(chlorobenzoyl)-p-methoxy-phenylhydrazine, 2-chloro-phenylhydrazine hydrochloride, 3-chlorophenyl-hydrazine hydrochloride, 4-chlorophenylhydrazine hydrochloride, cyclohexyl methylhydrazine, symdibenzoylhydrazine, 2,3-dichlorophenylhydrazine, 2,4-dichlorophenylhydrazine hydrochloride, 2,3-dichlorophenylhydrazine, 2,5-dichlorophenylhydrazine hydrochloride, 2,6-dichlorophenylhydrazine hydrochloride, 3,4-dichlorophenylhydrazine hydrochloride, 3,5-dichlorophenylhydrazine hydrochloride, 2,4-difluorophenylhydrazine hydrochloride, dihydrazine sulfate, 1,2-dimethylhydrazine dihydrochloride, 1,1-dimethylhydrazine (unsymmetrical), 2,3-dimethylphenylhydrazine hydrochloride, 2,4-dimethylphenylhydrazine hydrochloride, 2,5 dimethylphenylhydrazine hydrochloride, 2,6 dimethylphenylhydrazine hydrochloride, 3,4-dimethylphenylhydrazine hydrochloride, 3,5-dimethylphenylhydrazine hydrochloride, 2,4-dinitrophenylhydrazine, 1,1-diphenyihydrazine hydrochloride,(2-ethylphenyl)hydrazine hydrochloride, 4-ethylphenylhydrazine hydrochloride, 2-fluorophenylhydrazine hydrochloride, p-fluorophenyl hydrazine hydrochloride, 4-fluorophenyl hydrazine hydrochloride, anhydrous hydrazine, hydrazine base, hydrazine dihydrobromide, hydrazine dihydrochloride, hydrazine hydrate, hydrazine monoacetate, hydrazine monohydrobromide, hydrazine monohydro-chloride, hydrazine mononitrate, hydrazine oxygen scavenger, hydrazine solution, carbohydrazide, 1,5-diphenylcarbazide and 4-phenylsemicarbazide.

4. The process of claim 1, wherein said additive is hydrazine hydrate.

* * * * *